US00PP14961P2

(12) United States Plant Patent
Dofferhoff et al.

(10) Patent No.: US PP14,961 P2
(45) Date of Patent: Jun. 29, 2004

(54) ASTRANTIA PLANT NAMED 'ABBEY ROAD'

(50) Latin Name: *Astrantia major*
Varietal Denomination: Abbey Road

(76) Inventors: Johannes Adrianes Maria Dofferhoff, Middelburgseweg 1, 2811 PL Reenwijk (NL); Nicolaas Antonius Maria Rijnbeek, Reijerskoop 303, 2771 BL Boskoop (NL)

( * ) Notice: Subject to any disclaimer, the term of this patent is extended or adjusted under 35 U.S.C. 154(b) by 0 days.

(21) Appl. No.: 10/437,944

(22) Filed: May 13, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Astrantia plant named 'Abbey Road', characterized by its upright plant habit; dark colored stems and leaves; freely and continuous flowering habit; and inflorescences with showy involucral bracts that are dark purple in color.

2 Drawing Sheets

Botanical classification/cultivar designation: *Astrantia major* cultivar Abbey Road.

BACKGROUND OF THE INVENTION

The present Invention relates to a new and distinct cultivar of Astrantia plant, botanically known as *Astrantia major,* and hereinafter referred to by the cultivar name Abbey Road.

The new Astrantia originated from a cross-pollination in 1997 of two unidentified selections of *Astrantia major,* not patented. The new Astrantia was selected by the Inventors in May, 2002, in a controlled environment in Reenwijk, The Netherlands, from the resultant progeny on the basis of its dark purple-colored involucral bracts.

Asexual reproduction of the new cultivar by divisions harvested in Reenwijk, The Netherlands, has shown that the unique features of this new Astrantia are stable and reproduced true to type in successive generations.

SUMMARY OF THE INVENTION

Plants of the cultivar Abbey Road have not been observed under all possible environmental conditions. The phenotype may vary somewhat with variations in environment such as temperature and light intensity without, however, any variance in genotype.

The following traits have been repeatedly observed and are determined to be the unique characteristics of 'Abbey Road'. These characteristics in combination distinguish 'Abbey Road' as a new and distinct cultivar:

1. Upright plant habit.
2. Dark colored stems and leaves.
3. Freely and continuous flowering habit.
4. Inflorescences with showy involucral bracts that are dark purple in color.

Compared to plants of the parent selections, plants of the new Astrantia have thicker stems and darker colored leaves. In addition, plants of the new Astrantia and the parent selections differ in flower coloration as plants of the parent selections have greenish-white to light pink-colored flowers.

Plants of the cultivar Abbey Road can be compared to plants of the *Astrantia major* cultivar Ruby Wedding, not patented. In side-by-side comparisons conducted in Reenwijk, The Netherlands, plants of the new Astrantia differed from plants of the cultivar Ruby Wedding in the following characteristics:

1. Plants of the new Astrantia were taller than plants of the cultivar Ruby Wedding.
2. Plants of the new Astrantia had darker colored leaves than plants of the cultivar Ruby Wedding.
3. Plants of the new Astrantia had dark purple-colored involucral bracts whereas plants of the cultivar Ruby Wedding had dark red-colored involucral bracts.

BRIEF DESCRIPTION OF THE PHOTOGRAPHS

The accompanying colored photographs illustrate the overall appearance of the new Astrantia, showing the colors as true as it is reasonably possible to obtain in colored reproductions of this type. Colors in the photographs may differ slightly from the color values cited in the detailed botanical description which more accurately describe the colors of the new Astrantia.

The photograph on the first sheet comprises a side perspective view of typical flowering plants of 'Abbey Road' grown in an outdoor nursery.

The photograph on the second sheet is a close-up view of typical inflorescences of 'Abbey Road'.

DETAILED BOTANICAL DESCRIPTION

In the following description, color references are made to The Royal Horticultural Society Colour Chart, 2001 Edition, except where general terms of ordinary dictionary significance are used. Plants used in the aforementioned photographs and for the following description were grown under outdoor field conditions which closely approximate commercial production conditions in Reenwijk, The Netherlands. During the production of the plants, day temperatures ranged from 14 to 27° C. and night temperatures ranged from 7 to 14° C. Plants used for the photographs and description were about three years old. The photographs and description were taken in June, 2002.

Botanical classification: *Astrantia major* cultivar Abbey Road.

Parentage: Cross-pollination of two unidentified selections of *Astrantia major,* not patented.

Propagation:

*Type cutting.*—By divisions.

*Root description.*—Fine; very freely branching; brown in color.

Plant description:

*Form.*—Upright perennial flowering plant with basal rosette of leaves; numerous erect peduncles support umbels of flowers held well above the foliage.

*Plant height.*—About 85 cm.

*Plant diameter.*—About 55 cm.

*Vigor.*—Moderately vigorous.

*Branch description.*—Arrangement: Branching mostly basal; freely branching, about 20 basal branches develop per plant. Length: About 70 cm. Diameter: About 7 mm; thick. Strength: Strong. Texture: Smooth, glabrous. Color: 143A; towards the base, 144A; towards the apex, 143A with longitudinal stripes, 177B.

*Foliage description.*—Arrangement: Alternate, simple. Length: About 12 cm. Width: About 13.5 cm. Shape: Palmately-lobed. Apex: Acute. Base: Hastate. Margin: Doubly serrate. Texture, upper and lower surfaces: Smooth, glabrous. Venation: Laciniate. Petiole: Length: About 40 cm. Diameter: About 4 mm. Color: Developing foliage, upper surface: 137A. Developing foliage, lower surface: 137C. Mature foliage, upper surface: Slightly darker than 137A. Mature foliage, lower surface: 138B. Venation, upper surface: 143A to 143B. Venation, lower surface: 143B to 143C. Petiole color: 143A.

Inflorescence description:

*Inflorescence/flower appearance.*—Numerous, single, minute, upright, campanulate flowers subtended by showy involucral bracts; flowers arranged in compound umbels. Flowers face mostly upright to somewhat outwardly. Flowers not persistent.

*Quantity of flowers.*—Very freely flowering; during the flowering season, typically about 75 flowers per umbel and about 12 umbels per flowering stem will develop; therefore about 900 flowers per flowering stem and about 18,000 flowers develop per plant.

*Natural flowering season.*—Plants flower continuously from late May to mid-July in the Netherlands.

*Fragrance.*—None detected.

*Flower longevity on the plant.*—More than ten days.

*Flower longevity as a cut flower.*—About two weeks.

*Inflorescence length.*—About 5.5 cm.

*Inflorescence diameter.*—About 8 cm.

*Flower buds.*—Length: About 1.5 mm. Diameter: About 1 mm. Shape: Obovate; apex, flattened. Color: 143C to 143D, towards the apex, 59A.

*Flower diameter.*—About 1.5 mm.

*Flower depth* (*height*).—About 2 mm.

*Petals.*—Quantity per flower: About five. Length: About 2 mm. Width: About 0.7 mm. Shape: Narrowly elliptic. Apex: Acute. Margin: Entire. Texture, upper and lower surfaces: Smooth, dull. Color, both surfaces: 150D to lighter than 150D; central spot, 59A.

*Sepals.*—Quantity per flower: About five; rotate. Length: About 2 mm. Width: About 0.5 mm. Shape: Narrowly ovate. Apex: Acute. Base: Cuneate. Margin: Entire. Texture, upper and lower surfaces: Smooth, dull. Color, upper surface: 59A. Color, lower surface: 59A; towards the base, 138B.

*Involucral bracts.*—Quantity per inflorescence: About 16. Length: About 1.7 cm. Width: About 5 mm. Shape: Elliptic. Apex: Acute. Base: Cuneate. Margin: Entire or with two small teeth near the apex. Aspect: Mostly upright. Texture, upper and lower surfaces: Smooth; dull. Color, upper surface: N79B; towards the apex, N186A. Color, lower surface: Between 79A and 59A; towards the apex, N186A.

*Peduncles.*—Length: About 6 cm. Diameter: About 2 mm. Angle: Primary peduncles, erect; secondary and tertiary peduncles, about 30 to 40° from vertical. Strength: Strong. Color: 143A; towards the apex, overlain with N186A.

*Pedicels.*—Length: About 6 mm. Diameter: About 0.25 mm. Angle: About 0 to 60° from vertical. Strength: Strong. Color: 145C; towards the base, 186B.

*Inflorescences leaves.*—Arrangement: Subtending the inflorescence, typically about five leaves per inflorescence; sessile. Length: About 3.5 cm. Width: About 4 cm. Shape: Palmately lobed. Apex: Acute. Base: Cuneate. Margin: Entire with about three lobes. Color, upper surface: Between 147A and 202A; towards the base, 143C. Color, lower surface: 137C.

*Reproductive organs.*—Stamens: Quantity per flower: Typically five. Anther shape: Elliptic; dorsifixed. Anther size: About 1 mm by 0.25 mm. Anther color: 199B. Pollen amount: Scarce. Pollen color: 157C to 157D. Pistils: Quantity per flower: Typically two. Pistil length: About 3 mm. Style length: About 2.8 mm. Style color: N186A; towards the base, lighter than N186A. Stigma shape: Club-shaped. Stigma color: N186A. Ovary color: 142D.

*Fruits/seeds.*—Fruit and seed development has not been observed.

Disease/pest resistance: Plants of the new Astrantia have been noted to be resistant to pathogens and pests common to Astrantia.

Weather tolerance: Plants of the new Astrantia have been observed to be tolerant to rain and wind, are hardy to U.S.D.A. Zone 6, and tolerant to temperatures as high as 30° C.

It is claimed:

1. A new and distinct cultivar of Astrantia plant named 'Abbey Road', as illustrated and described.

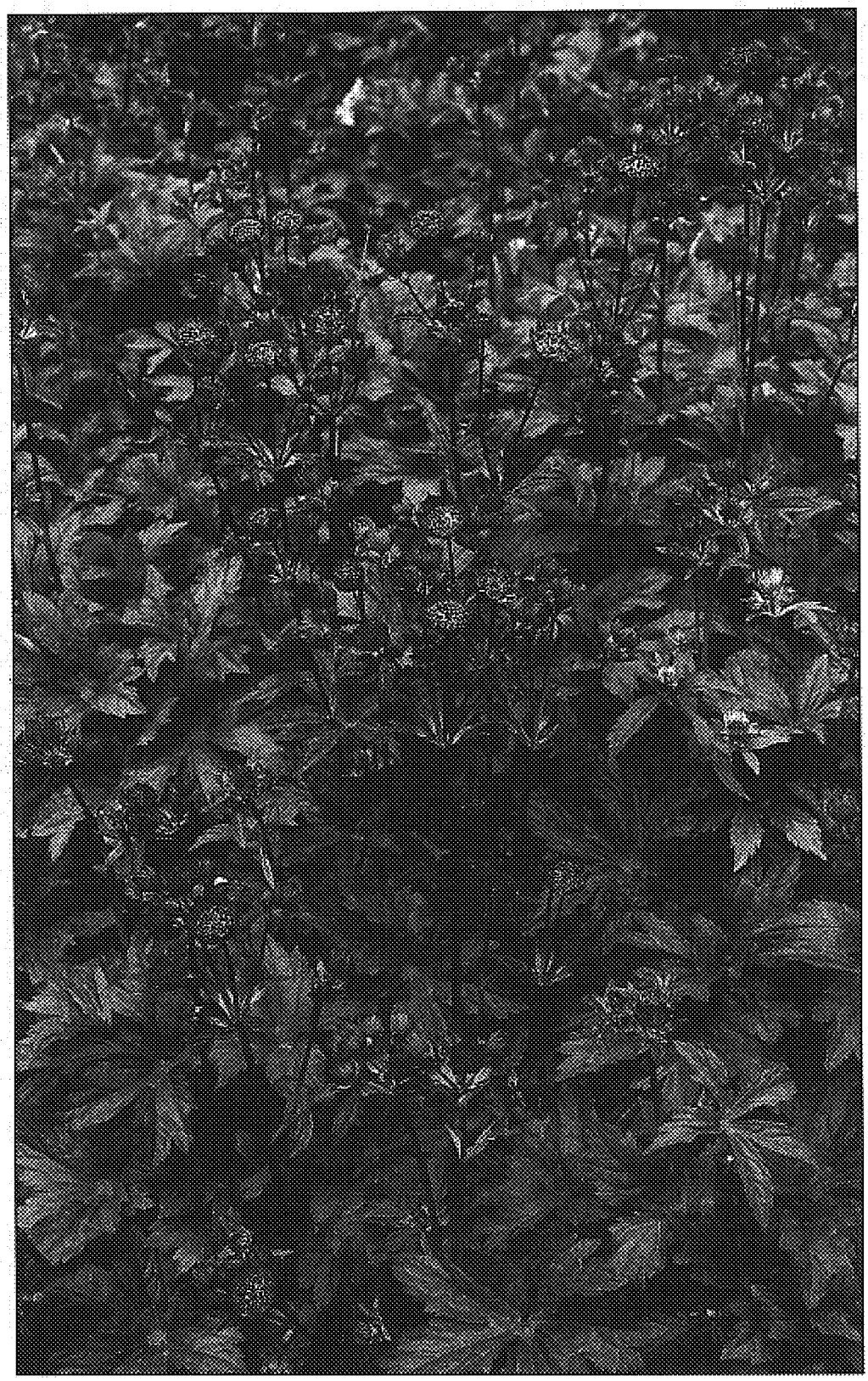

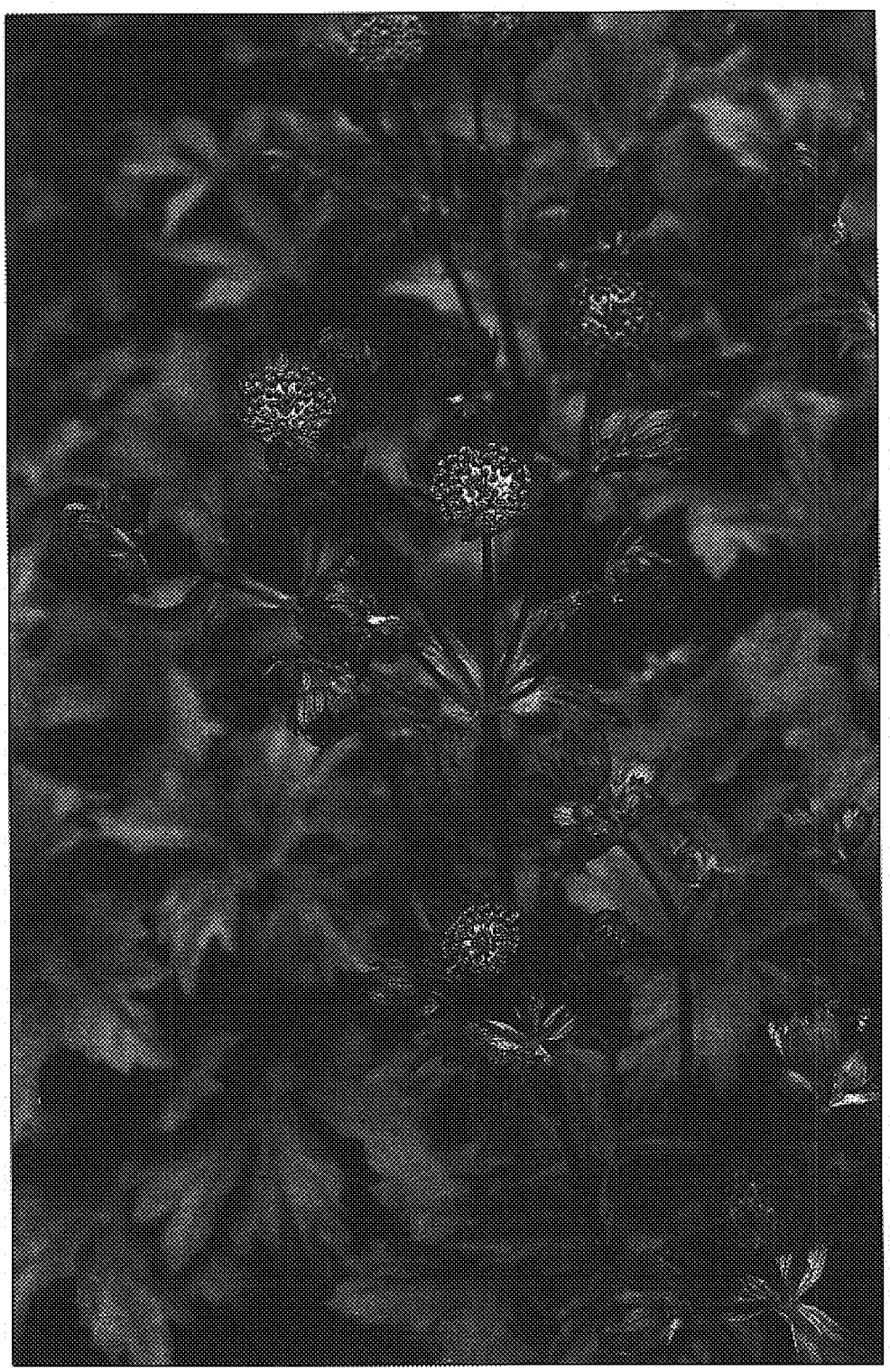

* * * * *